US00PP37439P2

(12) United States Plant Patent
Hansen

(10) Patent No.: US PP37,439 P2
(45) Date of Patent: May 26, 2026

(54) *EPIMEDIUM* PLANT NAMED 'Little Bo Peep'

(50) Latin Name: ***Epimedium* hybrid**
Varietal Denomination: Little Bo Peep

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,925

(22) Filed: Nov. 13, 2025

(51) Int. Cl.
*A01H 5/02* (2018.01)
*A01H 6/00* (2018.01)

(52) U.S. Cl.
USPC ..... Plt./429

(58) Field of Classification Search
USPC ..... Plt./429
See application file for complete search history.

(56) References Cited

U.S. PATENT DOCUMENTS

PP36,890 P2 * 8/2025 Hansen ..... Plt./429

* cited by examiner

*Primary Examiner* — Susan McCormick Ewoldt
*Assistant Examiner* — Zachariah Allan Kay

(57) ABSTRACT

A new cultivar of *Epimedium* plant named 'Little Bo Peep' characterized by its compact dense habit and semi-evergreen tri-parted foliage with ovate leaflets that develop as light chartreuse with bronze-burgundy blush in the cooler spring and become medium green in the summer. Medium-sized flowers appear on panicles above the foliage starting in late spring with spurs having a light pinkish-purple tips and medium rose-colored centers, and pinkish-purple sepals. 'Little Bo Peep' is useful in the garden landscape as a specimen, en mass, or in containers.

2 Drawing Sheets

Botanical denomination: *Epimedium* hybrid.
Variety designation: 'Little Bo Peep'.

STATEMENT REGARDING PRIOR DISCLOSURES UNDER 37 CFR 1.77(B)(6)

The Applicant asserts that no publications or advertisements relating to sales, offers for sale, or public distribution occurred more than one year prior to the effective filing date of this application. The first offer for sale was by Walters Gardens, Inc. on Nov. 13, 2024, to Garden State Growers. Walters Gardens, Inc. obtained the new plant and all information about the new plant directly from the inventor. Any information or disclosure about the claimed plant less than one year prior to the effective filing date of this application would have been obtained from directly or indirectly from the Inventor and would be a 35 U.S.C. 102(b) exception.

BACKGROUND OF THE INVENTION

The present invention relates to a new and distinct Barrenwort plant from the genus *Epimedium* and given the cultivar name 'Little Bo Peep'. The new plant was the result of a single seedling selection from a cross on Apr. 20, 2016, by the inventor between a proprietary selection of *Epimedium acuminatum* known as D-29 (not patented) as the female or seed parent and *Epimedium* X *youngianum* 'Be My Valentine' (not patented) as the male or pollen parent. The seeds were collected in May of 2016. The individually selected seedling was eventually given the breeder code 16-84-2 after being first isolated from trials at a nursery in Zeeland, MI in April of 2018. It was selected for the final introduction in April of 2020.

*Epimedium* 'Little Bo Peep' has been asexually propagated at the same nursery in Zeeland, MI by division of the rhizome in 2018 and found to reproduce plants that are identical and exhibit all the characteristics of the original plant in successive generations of asexual propagation.

*Epimedium* 'Little Bo Peep' has not been observed under all possible environments. The phenotype may vary slightly with different environmental conditions, such as temperature, light, fertility, moisture and maturity levels, but without any change in the genotype.

In comparison to the new plant, the female parent has smaller flowers spaced further apart, narrower sepals, and lighter pinkish-lavender spurs and more lanceolate foliage that is more bronze. The male parent has flower spurs that are a lighter pinkish color and deeper cherry red sepals.

The nearest comparison varieties known to the inventor are: 'Dark Beauty' (not patented), 'Pink Champagne' (not patented), 'Pink Parasol' (not patented), 'Pretty in Pink' (not patented).

'Dark Beauty' has flowers with pale pink spurs and dark rose sepals. 'Pink Champagne' has a larger habit in both height and width, longer lanceolate foliage with larger marginal teeth, and has larger flowers that have deeper raspberry-colored spurs and longer sepals. 'Pink Parasol' has a much larger habit and flowers with a dark rose spurs and medium pink sepals. 'Pretty in Pink' has a slightly taller habit and narrower sepals that are positioned further apart on the inflorescence.

*Epimedium* 'Little Bo Peep' is distinct from the parents and all other *Epimedium* known to the inventor in the following combined traits:

1. Compact, dense, semi-evergreen perennial;
2. Medium-sized flowers with pinkish-purple sepals, with spurs having a medium rose-colored center and light pink petals above the foliage beginning in late spring;
3. Foliage is tri-parted with ovate leaflets, light chartreuse with a bronze-burgundy blush in cooler conditions becoming medium green in the warmer summer.

BRIEF DESCRIPTION OF THE DRAWINGS

The photographs of the new *Epimedium* 'Little Bo Peep' plant demonstrate the overall appearance of the plant, including the unique traits. The colors are as accurate as reasonably possible with color reproductions. Ambient light spectrum, temperature, source, and direction may cause the appearance of minor variations in color.

DETAILED PLANT DESCRIPTION

Figure 1:
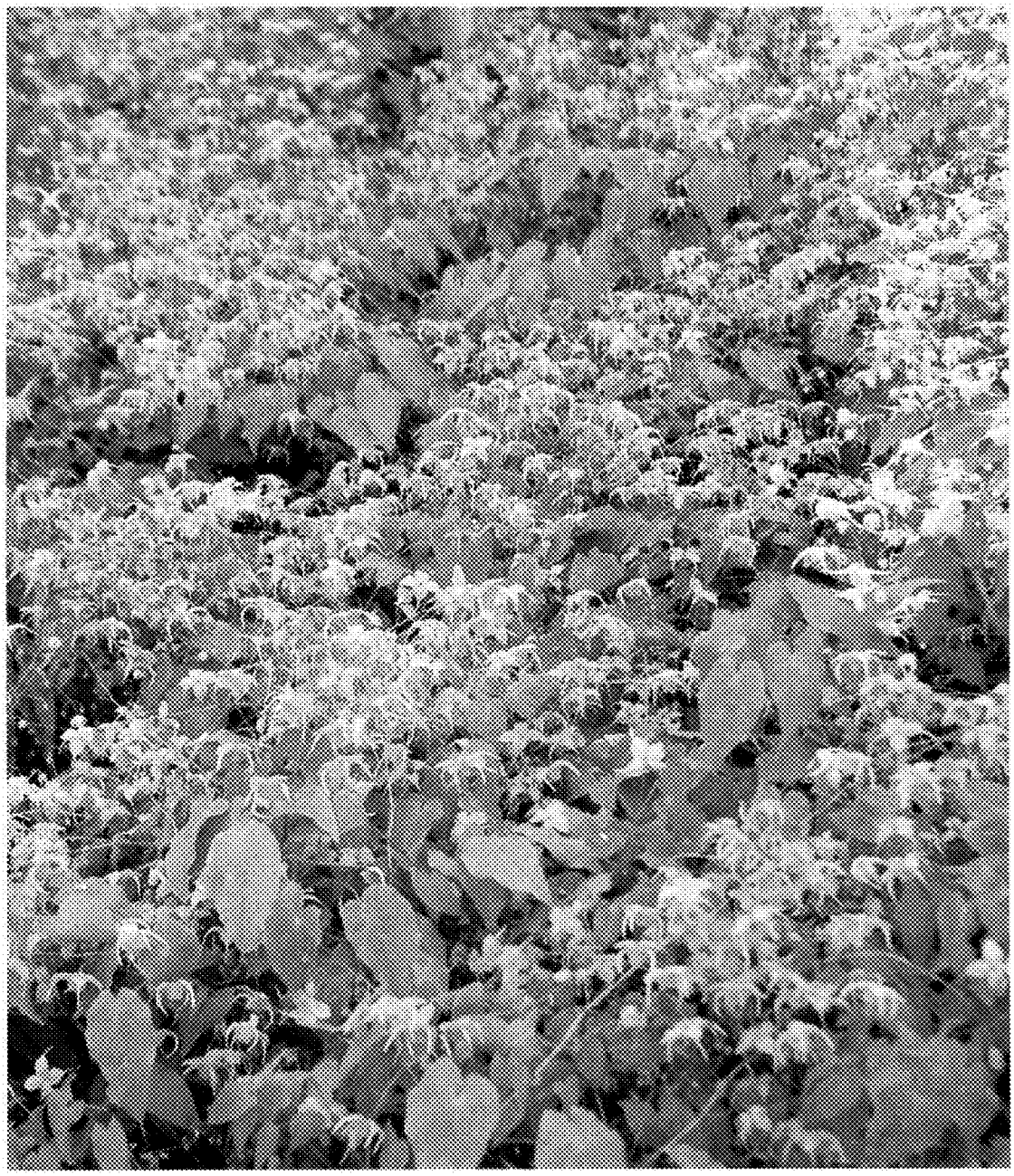
FIG. 1 shows a greenhouse view of a one-year-old plants in mid-season flower growing in containers at a nursery near Zeeland, Michigan.
Figure 2:
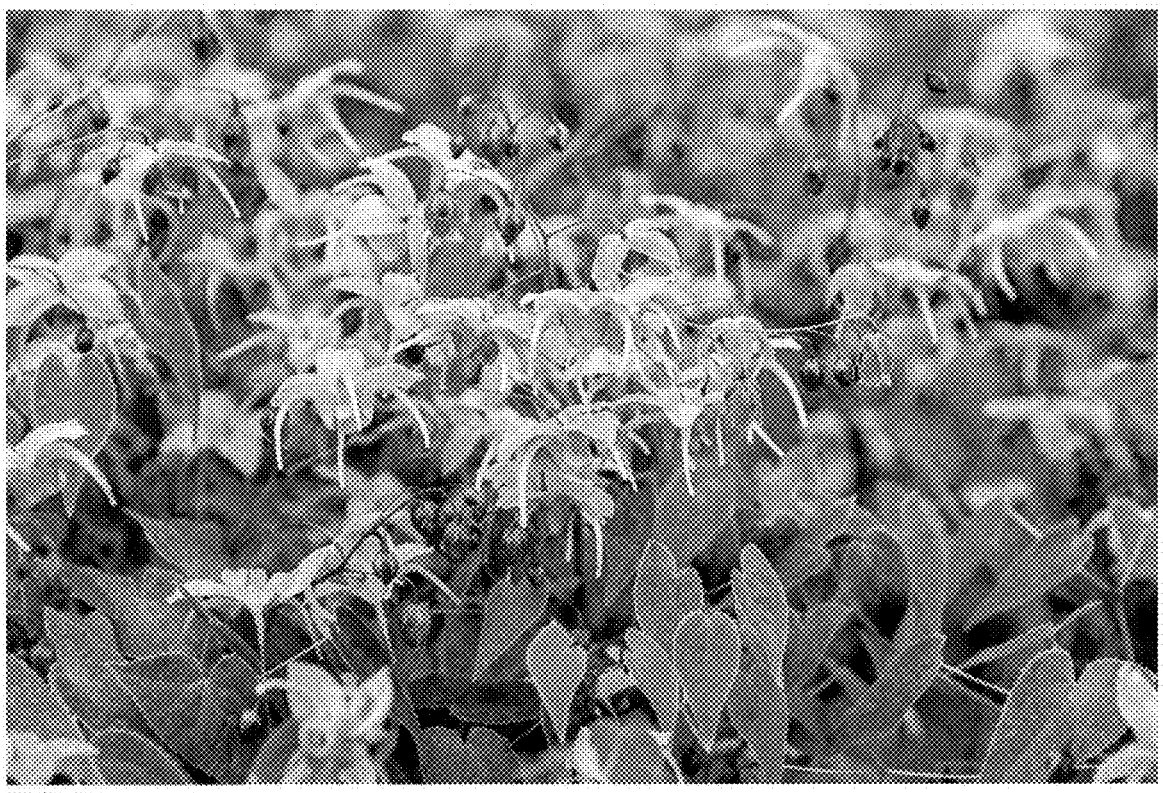
FIG. 2 shows a close-up of the scape with flowers and buds.

The following is a detailed description of the new *Epimedium* cultivar 'Little Bo Peep' based on observations of a two-year-old specimen grown in a shaded greenhouse in Zeeland, Michigan with supplemental watering and fertilizer as needed. Color descriptions are from the 2015 edition of The Royal Horticultural Society Colour Chart except where common dictionary terms are used.

Parentage: The female or seed parent is D-29, the male or pollen parent is 'Be My Valentine';

Propagation: Rhizome divisions;

Growth rate: Moderate;

Root development: Initiating in about 6 weeks;

Crop time: Finishing in a 3.8-liter pot from a 50 mm plug in 10 to 12 weeks;

Plant size: Soil level to top of foliar plane to about 36 cm tall and to about 68 cm wide, soil level to top of floral plane about 46 cm;

Root description: Dense, fibrous roots on rhizomes; color nearest RHS 161C;

Rhizomes: Surface smooth, matte, glabrous; to about 5 cm in length and 8 mm in width; color nearest RHS N170D;

Branching habit: Branches arise from rhizome;

Stem: Cylindrical; moderately glossy; sparsely micro-puberulent; strong; stiff; wiry; about 27 cm in length and 3 mm in diameter at base;

Stem color: Variable; proximally between RHS 176A and RHS 178A, and distally between RHS 146C and RHS 148B;

Stem aspect: Initially upright and arching with maturity;

Internode length: To 40 cm;

Leaf: Both cauline and from petiole arising from the soil; typically one per petiole or two to three per cauline node; tri-parted; to about 24 cm long and 23 cm wide;

Leaflet: Three; lanceolate; stiff; acute apex; cordate base, not overlapping; slightly undulate; finely serrulate with stiff, sharply-pointed, small spines variably in size 1 mm to 1.5 mm in length and 0.2 mm wide; center leaflet to 15.5 cm long and 7.5 cm wide, cordate base symmetrical with lobes to 3 cm long and 35 cm wide; side leaflets to 15 cm long and 8 cm wide, cordate base asymmetrical with outer lobe to 5.5 cm long and 4.5 cm wide, inner lobe to 2.8 cm long and 3.5 cm wide;

Leaflet surface: Adaxial smooth, glabrous, highly lustrous; abaxial micro-glabrescent to smooth and glabrous, matte;

Leaflet color: Young adaxial nearest RHS 177A with irregular patches 1 mm to 3 mm across of nearest RHS 144A; young abaxial nearest RHS 148C with a moderate to light blush of nearest RHS 177A; mature adaxial nearest RHS NN137B, mature abaxial between RHS191A and N138C;

Leaflet venation: Palmate; adaxial lightly indented; abaxial slightly costate; glabrous adaxial and abaxial; color adaxial nearest RHS 146C toward the margins and nearest RHS 148C toward the petiolule; abaxial midrib between RHS 150D and RHS 145D, primary veins nearest RHS 146D and secondary veins nearest RHS 137B;

Petioles: Arising from rhizome; cylindrical; smooth; slightly lustrous; stiff; to 40 cm long and 3 mm diameter;

Petiole color: Between RHS 181B and RHS 178B in the light exposed portions and nearest RHS 146D in portions protected from light;

Petiolules: Cylindrical; smooth; glabrous; slightly lustrous; stiff; to about 10 cm long and 1.5 mm diameter on center leaflets or side leaflets;

Petiolule color: Nearest RHS 160A;

Inflorescence: Compound corymb; flowering in the upper 22 cm and to about 16 cm wide; with about 9 branches, branches having about 8 flowers; inflorescence with about 40 flowers;

Flower timing: Beginning in late spring for about 3 weeks;

Flower buds one day prior to starting to open: Ovoid to conical, with an acute apex and round base; smooth, glabrous, about 7 mm long and 5 mm diameter;

Bud color one day prior opening: Sepal between RHS 176B and RHS 137A in the centers and the margins nearest RHS 186D, and exposed petals nearest RHS N186D;

Flower: Perfect; complete; actinomorphic;

Flower size: To about 30 mm across and 22 mm in depth;

Flower fragrance: None detected;

Lastingness of flowers: About 7 days from initial opening dehiscence; self-cleaning;

Petals: Four; lanceolate with basal spurs; arcuate outwardly and downwardly curving toward center axis; apex narrowly acute; base truncate, adnate on axial portion; adaxial and abaxial smooth, glabrous and slightly lustrous; to about 20 mm long natural, 25 mm long straightened, and about 7 mm across at base; spurs about 4 mm long and 5 mm across at base;

Petal color: When opening and fully the spur adaxial and abaxial is nearest RHS 76D heavily maculate with spots less than 0.0 mm diameter of between RHS 70B and RHS NN74C, except the distal 7 mm nearest RHS 76C;

Pedicel: Cylindrical; glabrous and slightly lustrous; to about 20 mm long and 0.3 mm diameter; average about 10 mm long and 0.3 mm diameter at base; aspect outwardly in proximal three-quarters and drooping downwardly in the distal one-quarter;

Pedicel color: Between RHS 174D and RHS 161B;

Peduncle: Cylindrical; stiff; strong; glabrous; slightly lustrous; main peduncle aspect upright to arching; with to about 10 branches in the upper region; branches outwardly about 45 degrees below main axis; to about 20 cm long and 2 mm diameter at base; branches to about 13 cm long and 1 mm diameter at base;

Peduncle color: Between RHS 146A and RHS 176B, with branch nodes nearest RHS 177A;

Sepals: Four; rotate; single whorl; ovate; smooth, glabrous and matte; attenuate base, acute apex; margin entire; to about 17 mm long and 9 mm across;

Sepal color: Adaxial and abaxial nearest RHS 76D heavily maculate with spots between RHS 70B and RHS NN74C;

Androecium: Four;

*Anther*.—Four; longitudinal; basifixed; extrose; oblong; to about 1 mm long and 1 mm across; color prior to opening nearest RHS 147A;

*Filaments*.—Four; applanate; about 4 mm long and 1 mm wide at base, narrowing distally; color in the proximal 1 mm nearest NN155D, distally nearest RHS 146A.

*Pollen*.—Not observed.

Gynoecium: Single; superior;

*Style*.—Cylindrical; glabrous; about 3 mm long and 0.3 mm diameter; color nearest RHS 145C.

*Stigma*.—Oblong; glabrous; to about.05 mm long and about 0.5 mm across; color nearest RHS 145C.

*Ovary*.—Oblong; glabrous; smooth; to about 3 mm long and 1 mm across; color between RHS 143A and RHS 143B.

Fruit/seeds: None observed to date.

Resistance: Not been tested or shown to be susceptible or resistance to pests and diseases common to *Epimedium;*

Hardiness: The new plant has survived USDA winter hardiness to at least zones 5 to 8 but has not been tested yet beyond these temperatures.

It is claimed:

1. A new and distinct cultivar of *Epimedium* plant named 'Little Bo Peep' as herein described and illustrated.

* * * * *